United States Patent [19]

Allen et al.

[11] Patent Number: 4,861,539
[45] Date of Patent: Aug. 29, 1989

[54] PROCESS OF MAKING WATER-ABSORBENT, WATER-INSOLUBLE, CROSS LINKED FIBER OR FILM

[75] Inventors: Adrian S. Allen, North Yorkshire; David Farrar; Peter Flesher, both of West Yorkshire, all of Great Britain

[73] Assignee: Allied Colloids Ltd., England

[21] Appl. No.: 123,571

[22] Filed: Nov. 20, 1987

[30] Foreign Application Priority Data

Nov. 20, 1986 [GB] United Kingdom ............... 8627729
Apr. 10, 1987 [GB] United Kingdom ............... 8708601
Apr. 10, 1987 [GB] United Kingdom ............... 8708600
Aug. 4, 1987 [GB] United Kingdom ............... 8718396

[51] Int. Cl.$^4$ .................. D01D 1/02; D01D 10/02
[52] U.S. Cl. .................... 264/204; 264/205; 264/210.2; 264/210.6; 264/210.8; 264/211; 264/211.13; 264/211.14; 264/236; 264/347
[58] Field of Search ............... 264/236, 347, 204, 205, 264/210.6, 210.2, 210.8, 211, 211.12, 211.13, 211.14

[56] References Cited

U.S. PATENT DOCUMENTS

| Re. 30,029 | 6/1979 | Smith | 128/285 |
|---|---|---|---|
| 2,764,498 | 9/1956 | Diamond | 264/211 |
| 2,955,437 | 12/1960 | Blombey | 264/211 |
| 3,082,056 | 3/1963 | Caldwell | 264/211 |
| 3,634,575 | 1/1972 | Serad | 264/211 |
| 3,926,891 | 12/1975 | Gross et al. | 260/29.6 E |
| 3,980,663 | 9/1976 | Gross | 128/156 |
| 4,041,121 | 8/1977 | Smith | 264/191 |
| 4,057,521 | 11/1977 | Gross | 425/264 |
| 4,066,584 | 1/1978 | Allen et al. | 264/191 |
| 4,076,673 | 2/1978 | Bukholder, Jr. | 264/204 |
| 4,104,214 | 8/1978 | Meierhoefer | 264/194 |
| 4,163,770 | 8/1979 | Porosoff | 264/211 |
| 4,218,692 | 8/1980 | Cremoux | 357/19 |
| 4,310,593 | 1/1982 | Gross | 264/204 |

FOREIGN PATENT DOCUMENTS 0213799 3/1987 European Pat. Off. .
2355923 1/1978 France .

Primary Examiner—Hubert Lorin
Attorney, Agent, or Firm—Ostrolenk, Faber, Gerb & Soffen

[57] ABSTRACT

Water absorbent, water insoluble, cross linked polymer fibre or film can be made by dry extrusion of a solution of a substantially linear polymer formed from a water soluble blend of monoethylenically unsaturated monomers comprising a plasticizing monomer, evaporating the solvent and forming polymeric fibre or film plasticized by an external plasticizer, stretching the fibre or film while the external plasticizer remains in the fibre or film, and then cross linking the polymer.

18 Claims, No Drawings

PROCESS OF MAKING WATER-ABSORBENT, WATER-INSOLUBLE, CROSS LINKED FIBER OR FILM

This invention relates to the production of water absorbent, water insoluble, polymeric fibre or film that is useful for absorbing aqueous fluids, for instance urine.

It is well known to provide by water absorbent, water insoluble, polymeric material in the form of particles by polymerising water soluble monomer or monomer blend, for instance acrylic acid, in the presence of a polyethylenically unsaturated monomer that will be copolymerised into the polymeric backbone so as to cause cross linking and render the polymer insoluble in water. Ionic cross linking, for instance by aluminium ions, between pendant groups is also known. Since the cross linking occurs substantially simultaneously with the polymerisation, the normal methods do not permit the polymer to be shaped by extrusion or coating techniques after polymerisation. Instead it is made in its desired final shape, e.g., as beads by reverse phase polymerisation, or in bulk form and is then comminuted to particles. There are, however, many instances where it would be desirable to be able to provide the polymer in the form of a film, fibre or other shaped element.

In U.S. Pat. Nos. 3,926,891, 3,980,663 and 4,057,521 various processes are described in which a substantially linear acrylic polymer is shaped and is then cross linked through its pendant groups. Film is made by casting a solution of the substantially linear polymer on a surface whilst fibre is made by extruding the solution into a bath of a ketone or chlorinated hydrocarbon followed by drying and cross linking. Various polymers are proposed for use in this process including, in U.S. Pat. No. 3,926,891, polymers made by saponification of a copolymer of alkyl (meth) acrylate, unsaturated carboxylic acid and, optionally, hydroxy alkyl acrylate. It appears that these processes have been commercially unsuccessful.

Another apparently unsuccessful proposal is made in FR No. 2,355,929. In this, a diol or diamine is mixed into an aqueous solution of a polymer which is then extruded as fibres which are then heated to cause cross linking. In the examples the polymer is generally polyacrylic acid but copolymers with alkyl, and hydroxy alkyl, acrylic acid esters are mentioned. A copolymer with 5% hydroxypropyl acrylate is exemplified.

For fibre or film production to be commercially successful it is necessary for it to be capable of being performed substantially continuously and at high speed. If the process is likely to result in frequent breakages of the fibre or film then it will not be suitable for commercial production. It seems that this may have been a problem in processes such as those described in FR No. 2,355,929. This is because optimum absorption characteristics suggest that the polymer should be a substantial homopolymer of polyacrylic acid (as free acid and/or salt) and yet such polymers are very brittle and we have found that it is substantially impossible to spin them reliably. Although softer copolymers are known, e.g., from U.S. Pat. No. 3,926,891, conventional handling techniques of these are still liable to lead to frequent breakages. Also these polymers are very unsatisfactory for use in diapers since the linear starting polymer is made by emulsion polymerisation, with the result that the polymer is contaminated with surfactant.

Probably for these various reasons, the above described processes have, apparently, not been commercialised. Instead, various other absorbent fibres and films have been made but their absorbency tends to be inferior, on a weight basis, relative to conventional particulate absorbents.

For instance one type of absorbent fibre is formed by hydrolysing the outer surfaces of polyacrylonitrile fibres so as to form a sheath of linear water soluble polymer and a core of insoluble polymer that gives the fibre strength. Another process comprises precipitating a water soluble polymer onto an insoluble substrate such as cotton (see e.g. U.S. Pat. Nos. 4,041,121 and 4,218,692). Another process involves injecting an aqueous solution of water soluble polymer into a stream of viscose just prior to extruding the viscose as a fibre or filament (see e.g. U.S. Pat. Nos. 4,066,584, 4,104,214 and Re 30,029). All these methods suffer from the disadvantage that the fibres incorporate a substantial amount of a material (polyacrylonitrile, viscose or cotton) that is of low absorbency and so the capacity of the fibres, on a weight basis, is relatively low compared to existing absorbent polymers. Also the soluble surface of many of the fibres tends to cause stickiness during use.

There remains an urgent need for fibres and films of water insoluble water swellable polymer that can be made reliably by large scale, high speed, manufacturing processes and that have satisfactory absorbency properties compared to the absorbency properties of conventional particulate water swellable polymers.

In the invention water absorbent, water insoluble, cross linked polymeric fibre or film is made by extruding into a gas atmosphere a solution in a solvent of a substantially linear polymer formed of a blend of monoethylenically unsaturated monomers and thereby evaporating the solvent and forming polymeric fibre or film, stretching the fibre or film, and then cross linking the polymer, and in this process the polymer fibre or film is permanently plasticised by inclusion of a plasticising monomer in the monomer blend and the fibre or film is additionally externally plasticised throughout the stretching by inclusion in the fibre or film of an external plasticiser that is dissolved in the substantially linear polymer.

Thus in the invention the polymer is permanently plasticised, after cross linking, as a result of having been formed from a blend of monomers including plasticising monomer, and the polymer is additionally further plasticised during the stretching by the inclusion of an external plasticiser that is dissolved in the linear polymer.

An important feature of the invention is that the polymer is initially formed in substantially linear form and is provided as an extrudable solution, this solution is dry extruded with sufficient evaporation of the solvent to precipitate the polymer and thereby form fibre or film (depending upon the shape of the extrusion orifice) while the polymer remains in its substantially linear form, the fibre or film is stretched while the polymer remains in its substantially linear form and the polymer is thereafter cross linked to a predetermined extent. Accordingly the cross linking system must be activatable after stretching the fibre or film and must be inert during and prior to the stretching.

Although the cross linking system can be a system that is activated by irradiation, for instance ultraviolet light, preferably it is a thermally activated system, in which event the rate of cross linking at the temperatures prevailing during the stretching and earlier stages of the process should be such that there is substantially no cross linking during these stages. By this means it is possible to optimise the stretching the fibre or film while the polymer is linear and then to fix the polymer in its stretched configuration by cross linking.

The substantially linear polymer is formed from a water soluble blend of monoethylenically unsaturated monomers that must, of course, be selected in known manner such that the final cross linked polymer is water absorbent. The monomer blend may be non-ionic, anionic or cationic, depending upon the liquids that are to be absorbed by the fibre or film. When a cationic monomer blend is to be used, this generally is formed of a mixture of a cationic monomer and a non-ionic monomer. Suitable cationic monomers are dialkylaminoalkyl (meth) -acrylates and -acrylamides, generally in the form of acid addition or quaternary ammonium salts. Any of the other cationic monomers that are suitable for incorporation into water absorbent, water insoluble, polymers can be used. Non-ionic monomer that may be included with the cationic monomers include (meth) acrylamide and any of the plasticising monomers discussed below.

Generally however the water soluble blend of monoethylenically unsaturated monomers is an anionic blend and comprises a carboxylic acid monomer, optionally with a non-ionic monomer. The monomers used in the invention may be allylic but are generally vinyl, most preferably acrylic monomers.

Suitable carboxylic monomers are (meth) acrylic acid or any of the other conventional ethylenically unsaturated carboxylic acids, optionally with 2-acrylamido-2-methyl propane sulphonic acid or any of the other conventional ethylenically unsaturated sulphonic acids, or allyl sulphonate. Carboxylic and sulphonic monomers may be present in the final polymer in free acid or water soluble salt form, suitable salts being formed with ammonia, amine or alkali metal. The proportion of salt and free acid groups can be adjusted after formation of the cross linked polymer or after polymerisation of the linear polymer or before polymerisation. Generally the ratio of free carboxylic acid/alkali metal or other salt carboxylic acid groups in the final polymer (and often also in the monomers that are used to form the linear polymer) from 1:1 to 1:10. The ratio is usually at least 1:2 and often 1:3. It is generally below 1:6 and often below 1:5.

When the cross linking reaction involves reaction with the carboxylic acid groups it is often preferred that some at least of the carboxylic acid groups should be present as free acid groups before the cross linking occurs. For instance, for this purpose, it may be adequate for 10 to 75%, preferably 25 to 75%, of the acid groups to be in free acid form before the cross linking occurs.

Although the linear polymer is generally made by polymerisation of carboxylic acid monomer (in free acid or salt form) it is also possible to make the polymer by polymerisation of monomer that can be subsequently reacted to form the carboxylic acid monomer. For instance the carboxylic acid (as free acid or salt form) groups that are to be present in the cross linked monomer may be present initially in the linear polymer in the form of hydrolysable ester groups, such as methyl ester groups, that can then be hydrolysed while in the form of a linear polymer to yield carboxylic acid (free acid or salt) groups.

The monomer blend must also include plasticising monomer, that is to say a monomer which results in the final polymer being more flexible and plasticised than it would be if the plasticising monomer had been replaced by a corresponding amount of the main absorbent monomer that is in the polymer, generally the anionic or cationic monomer.

Suitable plasticising monomers include aromatic ethylenically unsaturated monomers, such as acrylonitrile or styrenes (e.g., styrene or substituted styrenes), but they are preferably alkyl esters of (meth) acrylic acid or other suitable unsaturated carboxylic acid. Vinyl acetate and other vinyl esters may be used. The alkyl group of the ester generally contains less than 24 carbon atoms and usually 2 or more. Preferred alkyl groups contain 1 to 10 carbon atoms, especially ethyl and also higher alkyl groups such as 2-ethyl hexyl or other C6-C10 alkyl groups. Particularly preferred plasticising monomers are methyl or ethyl (meth) acrylate, butyl (meth) acrylate and 2-ethyl hexyl (meth) acrylate. They are generally present in amounts of at least 2% and preferably at least 10% since lower amounts tend to give inadequate benefit. The amount is usually below 50%, and generally below 45%, by weight based on the monomers used for forming the substantially linear polymer.

Other non-ionic monomers that may be used include ethylenically unsaturated monomers that carry a pendant group $-A_mB_nA_pR$ wherein B is ethyleneoxy, n is an integer of at least 2, A is propyleneoxy or butyleneoxy, m and p are each an integer less than n and preferably below 2 and most preferably zero, and R is a hydrophobic group containing at least 8 carbon atoms. The use of 1 to 50% by weight, generally 5 to 30% by weight, of such monomers can give plasticisation and can give improved absorptive capacity and non-tackiness, especially in aqueous electrolytes.

For a full description of suitable values of A, B, R, n, m and p, reference should be made to EP 0213799.

Hydroxyalkyl esters of ethylenically unsaturated carboxylic acids can also be included as plasticising monomer, the preferred esters being hydroxyalkyl (meth) acrylates. For optimum plasticisation the hydroxyalkyl group contains at least 6 carbon atoms, for instance 6 to 10 carbon atoms. They may be used, as plasticising monomers, in place of an equivalent amount of alkyl (meth) acrylate but, as explained below, the hydroxyalkyl (meth) acrylates can also be present to serve as internal cross linking agents.

When the polymer is cationic, the alkylene group in the described dialkylaminoalkyl group generally contains at least 2 carbon atoms, for instance 2 to 8 carbon atoms. The alkyl groups that are substituted onto the amino group generally contain 1 to 4 carbon atoms. Particularly preferred are dialkylaminoethyl (meth) acrylates and dialkylaminoalkyl (meth) acrylamides wherein the alkylene group is 1,3-propylene. However additional plasticisation can be obtained by selecting cationic groups in which the alkylene group and/or the alkyl substituents have larger numbers of carbon atoms, provided the monomer blend is still water soluble.

The substantially linear, water soluble, polymer may be formed from the monomer blend in any conventional manner. It may be pre-formed and then dissolved to form a polymer solution. For instance it may be made by reverse phase polymerisation if the monomer blend is soluble in water or by water-in-oil emulsion polymerisation if the blend is insoluble in the water, e.g., at a low pH. However this can incur the risk that the polymer may be contaminated by surfactant and this is undesirable. Preferably therefore the polymer is made by aqueous solution or other solution polymerisation methods. It may have been dried, but preferably not. Generally it is formed by solution polymerisation in the solvent in which it is to be extruded (generally water).

The polymerisation can be conducted in conventional manner in the presence of conventional initiators and/or chain transfer agents to give the desired molecular weight. If the molecular weight of the linear polymer is too low, the physical properties of the article may be inadequate. Generally therefore it is at least 30,000 and preferably at least 100,000 when the article is an extruded film or fibre but lower values, e.g., down to 10,000 or even down to 3,000 may be suitable in some shaping process, e.g., for casting or coating. If the molecular weight if too high it may be difficult to shape an adequately concentrated solution of the polymer as a fibre or film. Generally the molecular weight is below 1 million, usually below 500,000 and preferably below 250,000. However where the shaped article can initially be relatively thick, e.g., a coarse film or fibre that may then be stretched if it is desired to reduce its thickness, higher molecular weights, e.g., up to 10 million or more, are sometimes suitable.

The concentration of polymer in the solution is generally in the range 5 to 50% and will be selected, having regard to the molecular weight of the polymer, so as to give a solution having a viscosity that is convenient for extrusion through the spinnerette or other extrusion device that is to be used. Preferred viscosities are 20,000 to 50,000 cps measured by a Brookfield viscometer at 20rpm spindle 6 or 7 at 25° C. The concentration of polymer is usually at least 15%, with values of 20 to 40%, e.g., around 25 to 35%, often being suitable.

The solvent of the solution that is extruded is generally water but can be methanol or other suitable organic solvent or may be a blend of water and organic solvent. The solvent must be volatile so as to permit rapid evaporation after extrusion.

The linear polymer is cross linked after extrusion. The cross linking can be caused by reaction into the backbone of the linear polymer but preferably is by cross linking through pendant groups provided by one or more of the monomers that have been polymerised to form the linear polymer. The cross linking can be ionic, for instance as a result of exposing the linear polymer to any of the known ionic cross linking agents, preferably polyvalent metal compounds such as polyvalent aluminium compounds, for example aluminium sulphate. Organic compounds may be used instead of inorganic compounds to provide the cross linking.

Preferably however the cross linking is covalent between pendant groups in the linear polymer.

The covalent cross linking generally arises as a result of the formation of ester, amide (or imide) or urethane groups by reaction with carboxylic acid groups after extruding the polymer. Ester groups are preferred.

The reaction may be with an external cross linking agent or by internal cross linking, namely by reaction between reactive groups within the polymer.

When reaction is with an external cross linking agent the polymer may be extruded in the absence of the external cross linking agent and then exposed to the agent, for instance in gas form, during or after extrusion. For instance the polymer may be extruded into a gas containing the reagent. This will tend to give more cross-linking on the surface than in the centre of the article and whilst a gradation in the extent of cross-linking is desirable for some purposes, it is generally desirable that there should be a significant degree of cross-linking in the core of the article. Preferably therefore the reagent is a latent cross linking agent that is mixed throughout the fibre or film before the cross-linking reaction. The concentration of reagent throughout the fibre or film is preferably substantially uniform although a slight excess at the surfaces may be convenient.

The cross linking reaction may occur spontaneously upon contacting the linear polymer with the cross linking agent but generally has to be induced and so the latent or other cross linking reagent will be chosen having regard to the method of induction that will be available. Induction of cross linking can be by irradiation, for instance to ultra-violet light, but preferably is by heating, for example to a temperature in the range 150° C. to 300° C., generally 170° C. to 250° C.

If the reagent is only colloidally dispersed or emulsified into the polymer and its solution the cross linking is liable to be non-uniform, on a microscopic scale, and the reagent is likely to disrupt the polymeric structure during the stretching, and this can cause breakage. Preferably therefore the external reagent is wholly soluble in the polymer and in the polymer solution.

The cross-linking reagent should cross-link pendant groups in the polymer (generally carboxyl groups), rather than the polymer backbone, because it is undesirable to have to subject the shaped polymer to further polymerisation.

The reagent must be a stable, latent, reagent so that it does not react before shaping but can easily be made to react after shaping or, in some instances, after initial shaping but before final shaping. Suitable amounts are usually 1 to 15% by weight of polymer.

Urethane groups can be formed by use of a polyisocyanate (e.g. a diisocyanate) as the reagent. Better results are generally obtained by use of a polyamine that will react with the carboxylic groups to form amide linkages. The polyamine is any compound having at least two amino groups (secondary or primary) capable of reacting with carboxylic groups. Suitable polyamines are alkylene polyamines such as ethylene diamine, diethylene triamine, and hexamethylene diamine. Other suitable polyamines include melamine.

Polyamides that can be used include urea and biuret.

The reagent is preferably a reagent that will react with carboxylic acid groups in the linear polymer to form ester linkages. The reagent therefore is a polyfunctional reagent preferably containing hydroxyl and/or epoxide groups. Suitable polyepoxides are ethylene glycol diglycidyl ether and epoxy functional polyethers such as epoxidised polyethers of propylene oxide and/or ethylene oxide typically having molecular weights in the range 500 to 5000. Suitable polyhydroxy compounds include ethylene glycol, propylene glycol, diethylene glycol, glycerol, tripropylene glycol, sorbitol, penta-aerithrytol, and polyethylene glycols. Hydroxy epoxide compounds can be used.

Some external cross linking reagents, especially polymeric cross linking agents and polyhydroxy compounds such as glycols and glycerol, can serve as external plasticisers, as discussed below.

Because there can be a tendency for external plasticisers to migrate during the extrusion and stretching, with the result that the cross linking is then not entirely predetermined, it is often preferred to use internal cross linking. This may be achieved by forming the substantially linear polymer from a monomer blend that includes monomers having pendant groups that will react with each other upon appropriate heating after the extrusion. Any combination of monomers that will undergo such reaction can be used.

The reaction is generally best effected between a monomer that provides carboxylic acid monomer groups and monomers such as amides, epoxides and hydroxyl monomers. Reactions between some amides, especially substituted amides such as methylol acrylamide, and carboxylic groups can tend to be unstable and/or to give undesirable by-products (such as formaldehyde) and so preferably the internal cross linking is achieved by including in the monomer blend a monomer that provides carboxylic acid monomer groups and a monomer that provides hydroxyl groups that can react with the carboxylic acid groups to form ester cross linkages that contain only carbon and oxygen atoms in the linkages.

The monomer that provides hydroxylic groups for internal esterification with the carboxylic acid groups is selected from ethylenically unsaturated monomers that can react with carboxylic acid groups to form the desired ester linkages. The monomer must be one that does not form the ester cross links during the initial polymerisation to make the linear polymer, and that does not form any substantial number of cross links during the shaping of the linear polymer.

The hydroxyl groups may be generated in the linear polymer by, for instance, breaking a ring such as a glycidyl or epoxide substituted vinyl monomer, but preferred monomers contain free hydroxyl groups and are selected from vinyl alcohol, allyl alcohol and hydroxy alkyl esters of vinyl carboxylic monomers. The preferred esters are hydroxy alkyl esters of (meth) acrylic acid. The monomer may be monofunctional, containing a single hydroxyl group, or may be polyfunctional, containing two, three or more hydroxyl groups per vinyl group. The hydroxyl alkyl group generally contains from 1 to 10, preferably 1 to 8, carbon atoms. Suitable monomers include hydroxy ethyl (meth) acrylate, hydroxyl propyl (meth) acrylate, di- or tri- alkylene glycol mono (meth) acrylate where the alkylene group is ethylene or propylene, and glyceryl mono (meth) acrylate.

The amount of hydroxy monomer is preferably 0.1 to 15%, generally 1 to 10%, and the amount of carboxylic acid (or salt) is preferably above 50%, and often above 70%. These amounts are by weight based on total monomers. Often the blend is formed of 90-99% acrylic acid (some being in salt form) and 1 to 10% hydroxy alkyl acrylate.

Cross linking can be promoted by incorporating a catalyst in a solution of the polymer or by exposing the shaped polymer to a catalyst (e.g., by passing the polymer through an atmosphere or solution of a catalyst for the esterification reaction). Generally however the esterification is conducted in the absence of added catalyst. The monomers can be selected such that the esterification is effected by irradiation but generally it is effected by heating the shaped substantially linear polymer to a temperature above 150° C. for sufficient time for the cross linking reaction to occur. For instance it may be 170° C. to 200° C. for 5 to 40 minutes. At higher temperatures shorter reaction times are appropriate, for instance 0.1 to 10 minutes at 200° to 250° C. or up to 300° C. Preferred esterification conditions generally involve heating to 200° to 220° C. for, for instance, 1 to 3 minutes.

The fibre or film that is being stretched and taken to the cross linking position must contain external plasticiser, as well as the internal plasticiser provided by the monomer blend. The plasticiser needs to be soluble in the polymer as otherwise it is liable to disrupt the polymeric structure during the extrusion and stretching. The plasticiser may be a polyhydroxy compound or other compound known for plasticising polymers of the type involved in the invention. The polyhydroxy compound is preferably of molecular weight 100 to 2000 and most preferably is a polyethylene glycol of molecular weight 200 to 800, preferably about 400 to 600. Fatty esters of hydroxy or polyhydroxy compounds can be used, for instance the stearic ester of ethylene glycol or polyethylene glycol.

It is generally preferred that the final cross linked polymer should not contain migratable plasticiser, as this might migrate into the diaper or other environment around the final fibre or film. One way of achieving this is to use a plasticiser that participates in the cross linking reaction (e.g., a polyhydroxy compound). Preferably however the plasticiser is a volatile plasticiser and is evaporated from the polymer during or after the cross linking. The external, volatile plasticiser can be the solvent, or a component of the solvent, in the polymer solution. Preferably therefore the fibre or film still contains, after the stretching, sufficient of the initial solvent to plasticise it. Often the covalent cross linking is conducted after collecting the fibre or film, for instance into a roll or bundle, and it might have been expected that it would be essential for the fibre or film to be completely free of solvent at this stage, so as to minimise the risk of adjacent layers of film or fibre sticking to one another, but in the invention we find that it is satisfactory, and easily possible, to provide stretched fibre or film that is substantially non-tacky at its surface before it is cross linked, even though it contains, internally, sufficient residual solvent or other plasticiser to have a significant softening effect on the fibre or film. Achievement of this non-tacky surface depends, in part, on the substantially linear polymer being substantially free of monomer or oligomer having molecular weight substantially below the average molecular weight for the substantially linear polymer and thus the polymerisation should be conducted in known manner so as to give substantially no free monomer or oligomer in the polymer solution.

The amount of external plasticiser must be selected, depending upon the plasticiser being used, so as to give the desired softening and plasticising effect during the stretching and in the handling operations leading up to the cross linking reaction. In some instances it can be quite low, for instance down to 3% or 5% by dry weight of the fibre or film, but generally it is at least 10% based on the dry weight of the fibre or film. If the amount is too high the fibre or film is likely to be tacky and so generally the amount is below 80%, and usually below 50% based on the dry weight of polymer. These are the amounts at the end of the stretching process, before cross linking. When the plasticiser is volatile, the amount will be higher at the start of the stretching.

Extrusion of the solution is by dry spinning. The polymer is solidified upon extrusion, generally as a result of evaporation. The spinning is generally into warm air, optionally including an esterification or other catalyst for the cross linking.

The spinnerette may be heated but this is generally unnecessary since the degree of heating of the polymer solution as it passes through the spinnerette would tend to be insignificant. The spinnerette may have a slot shaped orifice for the production of film but generally has a large number of apertures, for the production of fibre. Adhesion of the fibres to themselves and to the spinnerette can be minimised in known manner, for instance by the use of a spinnerette having a non-stick surface such as of polytetrafluoroethylene and/or by application of spinning lubricants, in known manner.

The atmosphere into which the fibre or film is extruded must be sufficiently hot to evaporate the solvent so as to precipitate the polymer quickly but the combination of temperature and time as the film or fibre passes through this atmosphere must not result in any substantial cross linking. Generally the atmosphere is at a temperature of 150° to 300° C. often above 200° C. and typically 220° to 270° C., but as the fibre or film passes through this in a very short time, for instance a few seconds, substantially no cross linking occurs and volatile solvent will remain trapped in the fibres sufficient to give the desired plasticisation.

The fibre or film is stretched by being drawn away from the spinnerette in conventional manner, at a rate that gives the desired degree of stretching. This is selected according to the degree of orientation that is desired for the polymer molecules and generally involve the fibre or film being stretched to at least 1.5, and usually at least 2, times its original length. It can be stretched to a much higher degree if desired, for instance to the amount conventional in other synthetic polymer spinning processes.

The final fibre or film generally has a thickness or diameter below 250 $\mu$m and usually below 50 $\mu$m. Generally the fibre has a diameter typical of conventional synthetic polymer fibre diameters. It can be provided as continuous film or fibre (e.g., filament) or can be broken into shorter lengths, e.g., staple fibres typically having a length of 3 to 100 mm, or elements having a short major dimension, for instance not more than 1 mm, e.g., fibrids, lamellae or flakes.

The fibre or film usually has a gel capacity of at least 50 g deionised water, and at least 20 g 0.9% NaCl aqueous solution, per gram dry polymer.

The fibre or film may be provided with additional surface cross-linking, for instance ionic cross-linking with aluminium or other polyvalent metal compound, in order to improve its rate of absorption of liquids.

The resultant absorbent fibre or film may be used in any environment where it is desirable to absorb water, and in particular aqueous electrolyte such as urine or other body fluids, for instance as a replacement for part of the cellulosic fibres in diapers, catamenial appliances, incontinence pads or bandages. When the articles are in the form of fibres they may be scattered into the cellulosic fibres or a film or, preferably, a woven or non-woven fabric formed of the filaments or fibres may be incorporated in the diaper or other article.

Wound dressings, absorbent wipes and other fabrics may be formed from fibre or films part or all of which are made in accordance with the invention.

EXAMPLE 1

A copolymer comprising 69.4% by weight sodium acrylate, 17.6% by weight of acrylic acid, 3.0% by weight of hydroxypropyl methacrylate and 10% by weight of methyl acrylate was prepared as a 20% by weight solution in water. The viscosity of this polymer solution was 26,900 cps (Brookfield RVT at 20 rpm spindle 7 at 20° C.). A 100 micron thick film of this polymer cross linked in 2 minutes at 200° C. and 10 minutes at 180° C. to yield a material that absorbed about 200 times its own weight of water.

EXAMPLE 2

A copolymer was formed of 3% hydroxy propylmethacrylate, 40% methyl acrylate and 57% acrylic acid which was 75% sodium acrylate and 25% free acrylic acid. The polymer was made as an aqueous solution of about 35% polymer concentration, and had a molecular weight of around 500,000.

The viscous polymer solution was dry spun through a lubricated, multiple orifice, spinnerette into a temperature of about 250° C. and the fibres were stretched and immediately wound up. They were dry on the surface but contained residual moisture within their structure. Quite quickly after being spun the fibres were cured at 210° C. for 2 minutes. The resultant product was a flexible, high absorbent, fibre.

In alternative processes the amount of acrylate can be reduced to, for instance, 25% and/or methyl or other alkyl methacrylate can be used.

In another process polyethylene glycol of molecular weight 400 can be dissolved into the polymer solution, so as to provide additional external plasticisation.

EXAMPLE 3

A 20% solution in water of half neutralised polyacrylic acid having molecular weight of about 200,000 can be obtained by conventional solution polymerisation of a blend of acrylic acid and sodium acrylate with 20% 2-ethyl hexyl acrylate. About 5%, based on the polymer, epoxidised polypropylene oxide oligomer is dissolved into the solution and the solution can be extruded through an orifice into warm air. The resultant soft fibre can be drawn with a draw ratio of about 1.5:1 and wound while still slightly damp and then heated to cause cross linking.

The resultant fibre can be chopped into staple fibres and incorporated into the cellulosic fibrous pad of a diaper. It can have very high absorption capacity for water (typically about 300 grams per gram) but retains its fibrous structure even in the presence of excess water.

We claim:
1. A process of making water-absorbent, water-insoluble, cross linked polymer fibre or film having a gel capacity of at least 50 g deionized water per gram comprising extruding into a gas atmosphere a 5 to 50 weight percent solution in a solvent of a substantially linear polymer formed of a water soluble bend of monoethylenically unsaturated monomers and thereby precipitating the polymer by evaporation of the solvent and forming polymeric fibre or film, stretching the fibre or film and then cross linking the polymer in the stretched fibre or film, and in which the polymer fibre or film is permanently plasticised by inclusion of a plasticising amount of plasticising monomer in the monomer blend and the said solvent comprises an external plasticiser that is dissolved in the polymer of the fibre or film and that plasticises the fibre or film throughout the stretching and that is present in the stretched fibre or film in a plasticising amount and that comprises a volatile liquid, and in which the volatile liquid is evaporated during or after the cross linking.

2. A process according to claim 1 in which the external plasticiser is solvent from the polymer solution.

3. A process according to claim 1 in which the polymer solution is an aqueous solution and the external plasticiser comprises water.

4. A process according to claim 1 in which the amount of external plasticiser in the said stretched fibre or film is at least 10% based on the dry weight of the fibre or film.

5. A process according to claim 1 in which the stretched fibre or film is substantially non-tacky before it is cross linked and while it still contains the external plasticiser and the drawn fibre or film is collected and is then cross linked.

6. A process according to claim 1 in which the external plasticiser comprises material that is reactive with the linear polymer and is reacted into the polymer during cross linking.

7. A process according to claim 1 in which the monomer blend includes 10 to 50% by weight of a plasticising monomer selected from the group consisting of styrenes, vinyl esters, acrylonitrile and alkyl- and hydroxyalkyl- esters of ethylenically unsaturated acids.

8. A process according to claim 1 in which the monomer blend comprises carboxylic acid monomer and the cross linking is covalent cross linking.

9. A process according to claim 1 in which cross linking is effected by reaction between the substantially linear polymer and a cross linking reagent dissolved in the polymer solution and which is soluble in the polymer.

10. A process according to claim 1 in which the cross linking is by reaction between pendant groups derived from different monomers of the monomer blend.

11. A process according to claim 1 in which the monomer blend comprises monomer that provides carboxylic acid monomer groups and monomer that provides hydroxyl groups that can react with the carboxylic acid groups and the cross linking is by the formation of ester groups between the carboxylic and hydroxylic groups.

12. A process according to claim 1 in which the polymer is extruded in the form of a fibre.

13. A process according to claim 1 in which the polymer is extruded in the form of a film.

14. A process of making water-absorbent, water-insoluble, cross linked polymer fibre or film having a gel capacity of at least 50 g deionized water per gram comprising extruding into a gas atmosphere a 5 to 50 weight percent aqueous solution of a substantially linear polymer formed of a water soluble blend of a monoethylenically unsaturated monomers comprising carboxylic acid monomer and a plasticising amount of a plasticising monomer sufficient to permanently plasticise the fibre or film in a solvent and thereby precipitating the polymer by evaporation of the solvent and forming polymeric fibre or film, stretching the fibre or film to form stretched fibre or film, the water of said solvent comprising an external plasticiser that is dissolved in the polymer of the fibre or film and that plasticises the fibre or film throughout the stretching and that is present in the stretched fibre or film in a plasticising amount of at least 10% based on the dry weight of the fibre or film, collecting substantially non-tacky stretched fibre or film still containing external plasticiser, covalently cross linking the stretched fibre or film, and in which water is evaporated during or after the cross linking.

15. A process according to claim 14 in which the said blend consists essentially of carboxylic acid monomer and 10 to 50% by weight of a plasticising monomer selected from the group consisting of styrenes, vinyl esters, acrylonitrile and alkyl- and hydroxylalkyl- esters of ethylenically unsaturated acid.

16. A process according to claim 15 in which the said blend contains 1 to 15% hydroxyalkyl (meth) acrylate.

17. A process according to claim 16 in which the polymer is extruded in the form of a fibre.

18. A process according to claim 16 in which the polymer is extruded in the form of a film.

* * * * *